(12) United States Patent
Takahashi et al.

(10) Patent No.: US 9,123,156 B2
(45) Date of Patent: Sep. 1, 2015

(54) X-RAY CT APPARATUS AND IMAGE RECONSTRUCTION METHOD

(75) Inventors: Hisashi Takahashi, Tokyo (JP); Taiga Goto, Tokyo (JP); Koichi Hirokawa, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 207 days.

(21) Appl. No.: 13/824,697

(22) PCT Filed: Oct. 13, 2011

(86) PCT No.: PCT/JP2011/073473
§ 371 (c)(1),
(2), (4) Date: Mar. 18, 2013

(87) PCT Pub. No.: WO2012/050149
PCT Pub. Date: Apr. 19, 2012

(65) Prior Publication Data
US 2013/0177132 A1    Jul. 11, 2013

(30) Foreign Application Priority Data
Oct. 14, 2010 (JP) .................. 2010-231840

(51) Int. Cl.
*G06T 11/00*    (2006.01)
*G01N 23/04*    (2006.01)
(Continued)

(52) U.S. Cl.
CPC .............. *G06T 11/006* (2013.01); *A61B 6/032* (2013.01); *A61B 6/5205* (2013.01); *A61B 6/5264* (2013.01); *G06T 2211/424* (2013.01)

(58) Field of Classification Search
CPC .. A61B 6/5205; G01N 23/046; G06T 11/006; G06T 11/008; G06T 2211/424
USPC ............................................................ 378/4
See application file for complete search history.

(56) References Cited

U.S. PATENT DOCUMENTS 5,414,623 A * 5/1995 Lu et al. ................ 382/131
5,907,594 A    5/1999 Lai
(Continued)

FOREIGN PATENT DOCUMENTS

JP    2001-509400    7/2001
JP    2002-065663    3/2002
(Continued)

OTHER PUBLICATIONS

International Search Report in PCT/JP2011/073473.

*Primary Examiner* — Glen Kao
*Assistant Examiner* — Dani Fox
(74) *Attorney, Agent, or Firm* — Cooper & Dunham LLP

(57) ABSTRACT

In order to provide an X-ray CT apparatus and the like that reconstruct an image using an iterative approximation method which ensures stable convergence and can be executed at high speed, a computation device 5 of an X-ray CT apparatus 1 calculates matrices A, B, D, R, and R' on the basis of the scanning conditions input through an input device 6 (step 1). Then, the computation device 5 calculates each element of a matrix $I-\alpha(SB^{T}DA+\beta SR)$ (step 2). Then, the computation device 5 calculates the operator norm $\|I-\alpha(SB^{T}DA+\beta SR)\|$ of the matrix $I-\alpha(SB^{T}DA+\beta SR)$ (step 3). Then, the computation device 5 determines a relaxation coefficient $\alpha$ such that a predetermined conditional expression is satisfied (step 4).

12 Claims, 12 Drawing Sheets

(51) Int. Cl.
*A61B 6/03* (2006.01)
*A61B 6/00* (2006.01)

(56) References Cited

U.S. PATENT DOCUMENTS 5,909,476 A * 6/1999 Cheng et al. .................. 378/4
6,101,236 A * 8/2000 Wang et al. .................. 378/4
6,798,860 B1 9/2004 Hsieh et al.
2006/0067461 A1 3/2006 Yin et al.

FOREIGN PATENT DOCUMENTS

JP 2006-105975 4/2006
JP 2010-136958 6/2010
WO WO2010/016425 A1 2/2010

* cited by examiner

FIG.6
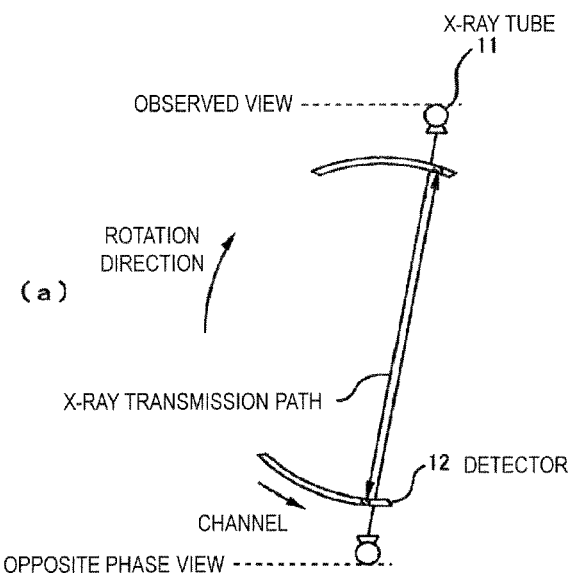
(a)
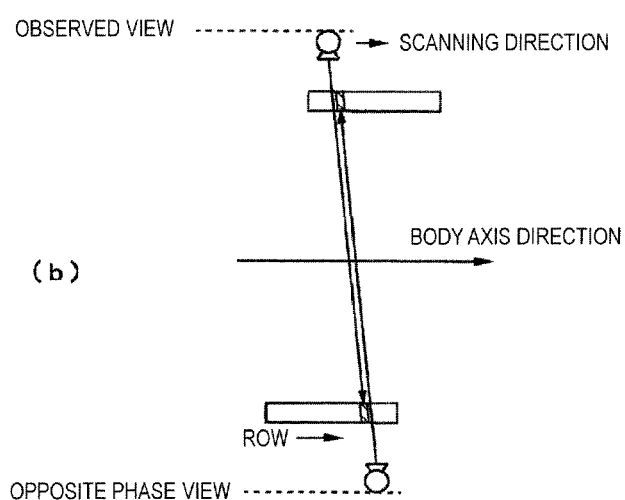
(b)

X-RAY CT APPARATUS AND IMAGE RECONSTRUCTION METHOD

TECHNICAL FIELD

The present invention relates to an X-ray CT apparatus that reconstructs an image using an iterative approximation method.

BACKGROUND ART

The X-ray CT apparatus is an apparatus that obtains a tomographic image of an object by irradiating the object with fan-beam shaped X-rays or cone-beam shaped X-rays (conical or pyramid beam shaped X-rays), measuring X-rays transmitted through the object using an X-ray detector, and reconstructing the measurement data from multiple directions.

Image reconstruction methods in the X-ray CT apparatus are largely divided into an analysis method and an iterative approximation method. The analysis method is a method of solving a problem analytically on the basis of a projection cutting plane theorem. The iterative approximation method is a method of mathematically modeling an observation system that has acquired the projection data and estimating the best image with a repetition method on the basis of the mathematical model.

When both methods are compared, the advantage of the analysis method is that the amount of computation is overwhelmingly small since a reconstructed image is directly obtained from the actual projection data. On the other hand, the advantage of the iterative approximation method is that the quantum noise on the image or artifacts (such as cone beam artifacts) generated in the analysis method can be reduced since the physical process up to the acquisition of projection data and statistical fluctuations included in the actual projection data can be considered as a mathematical model and a statistical model, respectively.

Conventionally, as an image reconstruction method in multi-slice CT, the Feldkamp method that is an analysis method or an improved method of the Feldkamp method has been mainly used due to the small amount of computation. However, practical applications of the iterative approximation method are also beginning to be considered with the development of high-performance computers in recent years.

The iterative approximation method is a method of setting the evaluation index of an image in advance and updating the image iteratively so that the evaluation value obtained by quantifying the evaluation index takes a maximum or minimum value. As the evaluation index, discrepancy between actual projection data and forward projection data obtained by converting an image into projection data in the update process, stochastic plausibility, or the like is used. A function for calculating the evaluation value is called an evaluation function.

An iterative approximation method using a penalized weighted least-square error function as an evaluation function has been proposed in NPL 1. In the methods proposed up to now, matrices that are transposed matrices of each other in forward projection processing and back projection processing are generally applied as proposed in NPL 1.

On the other hand, although there are few methods, iterative approximation methods to apply matrices that are not transposed matrices of each other in forward projection processing and back projection processing have also been proposed. A method of performing iterative update by applying a view-direction weight to the back projection processing has been proposed in NPL 2.

Hereinafter, the back projection processing in which the view-direction weight is used is called "view-direction weighted back projection processing".

The view-direction weighted back projection processing itself has been proposed in NPL 3, and is a technique used in the analysis method. The view-direction weighted back projection processing has the following advantages.

(1) Redundancy of projection data can be eliminated.
(2) Time resolution can be improved.

When matrices that are not transposed matrices of each other in the forward projection processing and the back projection processing are applied, a relaxation coefficient related to the speed and stability of convergence in the iterative approximation method is included in the update expression for iterative update. It is necessary to set the relaxation coefficient in a specific range for stable convergence in the iterative approximation method.

NPL 2 discloses that the relaxation coefficient is determined experientially. On the other hand, a method of calculating the relaxation coefficient using a power law has been proposed in NPL 4. The power law is an iterative solution technique to calculate the maximum eigenvalue of a certain matrix.

Meanwhile, when a spiral scan is performed at high bed movement speed, actual projection data in a row direction is insufficient. Accordingly, there is a problem in that the region where an image is obtained by the iterative approximation method is restricted.

In order to solve this problem, PTL 1 discloses a method of generating virtual row data and virtual channel data by extending actual projection data and then performing back projection processing in the analysis method. If the method disclosed in PTL 1 can be applied to the iterative approximation method, it is possible to relax the restriction of the region.

Hereinafter, the processing of generating virtual row data and virtual channel data by extending actual projection data as in the method disclosed in PTL 1 is called "data extension type back projection processing".

CITATION LIST

Patent Literature

[PTL 1] JP-A-2009-90139

Non Patent Literature

[NPL 1] H. Erdogan et. al., "Ordered subsets algorithms for transmission tomography," Phys. Med. Biol., Vol. 44, pp. 2835-2851, 1999

[NPL 2] J. Sunnegardh, "Combining analytical and iterative reconstruction in helicalcone-beam CT," "Linkoping Studies in Science and Technology Thesis No. 1301, 2007

[NPL 3] S. Wesarg et. al., "Parker weights revisited," Med. Phys. Vol. 29, No. 3, pp 372-378, March 2002

[NPL 4] G. L. Zeng and G. T. Gullberg, "Unmatched projector/backprojector pairs in an iterative reconstruction algorithm" IEEE. Trans. Med. Imag, Vol. 19, No. 5, pp 548-555, May 2000

SUMMARY OF INVENTION

Technical Problem

The problem that has not been solved by the methods in the related art and that the present invention is trying to solve is as follows.

In a scanning of the X-ray CT apparatus, a scanning time difference occurs in the view direction of actual projection data since the data is collected while rotating the X-ray tube and the X-ray detector. For this reason, when an object moves during a scan, actual projection data having different positional information in the view direction is collected. When an iterative approximation method is applied to such data using matrices that are transposed matrices of each other in forward projection processing and back projection processing, an image reflecting the discrepancies due to the movement of the object is reconstructed as optimal image. As a result, since the degradation of image quality due to the movement is caused in the obtained image, a certain correction method is required.

The degradation of image quality due to the movement of an object can be reduced by using the view-direction weighted back projection processing in the iterative approximation method, as in the method disclosed in NPL 2. In the method disclosed in NPL 2, however, there is a problem caused by an operator determining the relaxation coefficient experientially.

A sufficient condition of the relaxation coefficient for the convergence in the iterative approximation method changes depending on the bed movement speed, scanning FOV (Field Of View), or the like as scanning conditions. It is very cumbersome and time consuming that the operator determines the relaxation coefficient experientially depending on a large number of these scanning conditions.

In addition, generally, if the relaxation coefficient is set as a small value, the convergence condition of iterative approximation processing is satisfied regardless of scanning conditions due to the characteristic of the update matrix. However, if a too small relaxation coefficient is set, convergence of iterative approximation processing becomes slow. As a result, the quality of a reconstructed image is also degraded.

In addition, when the relaxation coefficient is determined using the power law as in the method disclosed in NPL 4, convergence in the iterative approximation method itself is stable since the relaxation coefficient is automatically calculated according to the scanning conditions. In the method disclosed in NPL 4, however, since the number of dimensions of actual projection data and images to be used for the image reconstruction of the X-ray CT apparatus is enormous, it is necessary to calculate large matrix operations iteratively. As a result, computation time is increased.

In addition, when the data extension type back projection processing of the method disclosed in PTL 1 is applied to the back projection processing of the iterative approximation method, matrices that are not transposed matrices of each other in the forward projection processing and the back projection processing are applied in the back projection processing. Then, it is necessary to set the optimal value for the relaxation coefficient in the same manner as in NPL 2 and NPL 4. That is, there is a problem in that computation time is increased if an optimal value is not set as the relaxation coefficient.

The present invention has been made in view of the above-described problem, and it is a first object of the present invention to provide an X-ray CT apparatus and the like that reconstruct an image using an iterative approximation method which ensures stable convergence and can be executed at high speed. A second object is to provide an X-ray CT apparatus and the like capable of suppressing the degradation of image quality when the iterative approximation method is applied to the data including the body movement. A third object is to provide an X-ray CT apparatus and the like capable of suppressing the degradation of image quality when the iterative approximation method is applied under the scanning conditions in which data loss occurs at the time of an axial scan or a spiral scan of high bed movement speed.

Solution to Problem

In order to achieve the above-described object, a first invention is an X-ray CT apparatus that reconstructs a tomographic image of an object using an iterative approximation method to apply matrices that are not transposed matrices of each other in forward projection processing and back projection processing. The X-ray CT apparatus includes: a scanning unit that acquires actual projection data of the object on the basis of scanning conditions; and a computation unit that reconstructs the tomographic image by performing iterative approximation on the actual projection data using the scanning conditions and an update expression of the iterative approximation method including a relaxation coefficient that determines convergence of computation. The relaxation coefficient is analytically calculated on the basis of the scanning conditions.

A second invention is an image reconstruction method of reconstructing a tomographic image of an object using an iterative approximation method to apply matrices that are not transposed matrices of each other in forward projection processing and back projection processing. The image reconstruction method includes: a step of acquiring actual projection data of the object on the basis of scanning conditions; and a step of reconstructing the tomographic image by performing iterative approximation on the actual projection data using the scanning conditions and an update expression of the iterative approximation method including a relaxation coefficient that determines convergence of computation. The relaxation coefficient is analytically calculated on the basis of the scanning conditions.

Advantageous Effects of Invention

According to the present invention, it is possible to provide an X-ray CT apparatus and the like that reconstruct an image using the iterative approximation method which ensures stable convergence and can be executed at high speed. In addition, it is possible to provide an X-ray CT apparatus capable of suppressing the degradation of image quality when the iterative approximation method is applied to the data including the body movement. In addition, it is possible to provide an X-ray CT apparatus and the like capable of suppressing the degradation of image quality when the iterative approximation method is applied under the scanning conditions in which data loss occurs at the time of an axial scan or a spiral scan of high bed movement speed.

BRIEF DESCRIPTION OF DRAWINGS

FIG. 6 is a diagram illustrating a correlation between an observed view and an opposite phase view.

DESCRIPTION OF EMBODIMENTS

Hereinafter, embodiments of the present invention will be described in detail on the basis of the drawings. First, the configuration of an X-ray CT apparatus 1 and the process of the X-ray CT apparatus 1, which are common to all the embodiments, will be described with reference to FIGS. 1 to 3.

Figure 1:
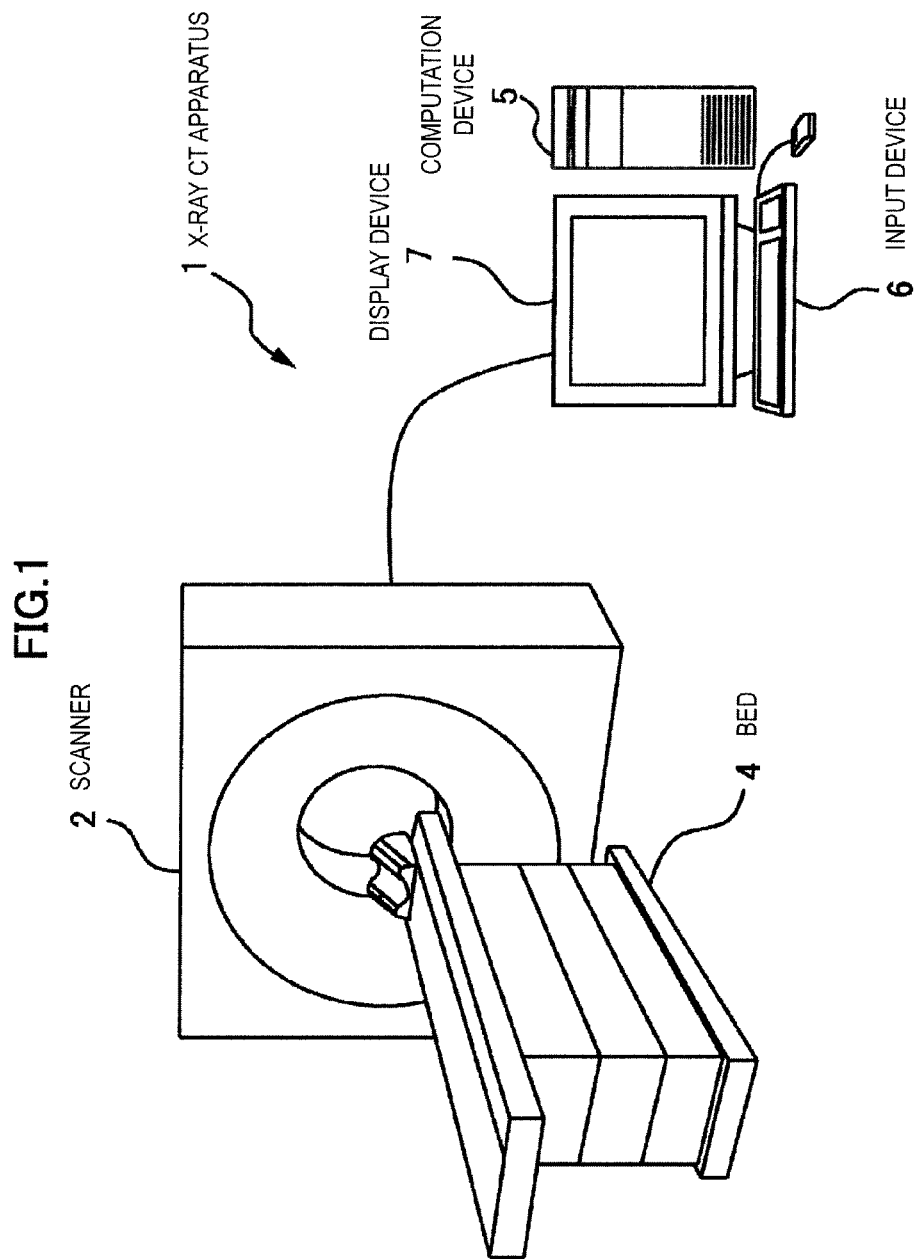
FIG. 1 is an external view of an entire X-ray CT apparatus 1.

As shown in FIG. 1, the X-ray CT apparatus 1 includes a scanner 2 (scanning unit) in which an X-ray tube 11 and a detector 12 are mounted, abed 4 on which an object 10 is placed, a computation device 5 (computation unit) that performs processing on the data obtained from the detector 12, an input device 6 such as a mouse, a track ball, a keyboard, and a touch panel, and a display device 7 that displays a reconstructed image and the like.

An operator inputs scanning conditions, reconstruction parameters, or the like through the input device 6. Examples of the scanning conditions include bed movement speed, tube current, tube voltage, and slice position. In addition, examples of the reconstruction parameters include a region of interest, reconstructed image size, back projection phase width, and a reconstruction filter function.

Figure 2:
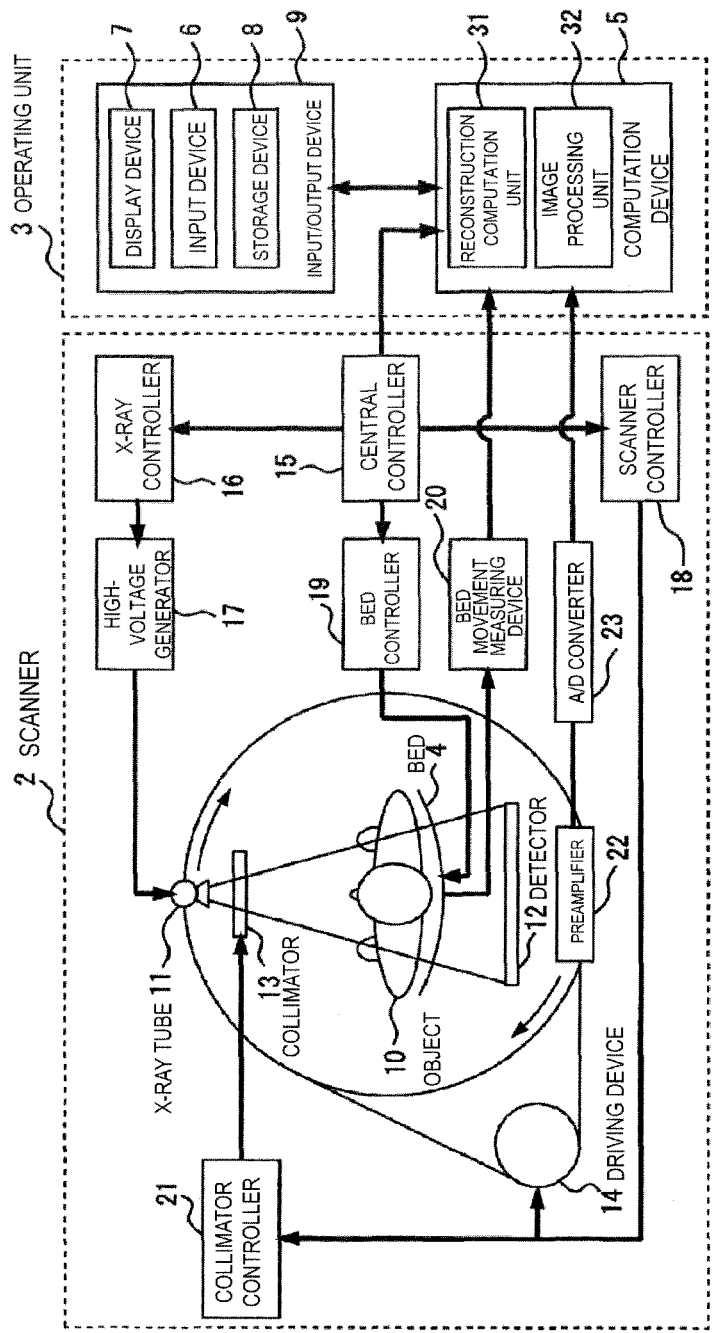
FIG. 2 is a block diagram of the X-ray CT apparatus 1.
Figure 3:
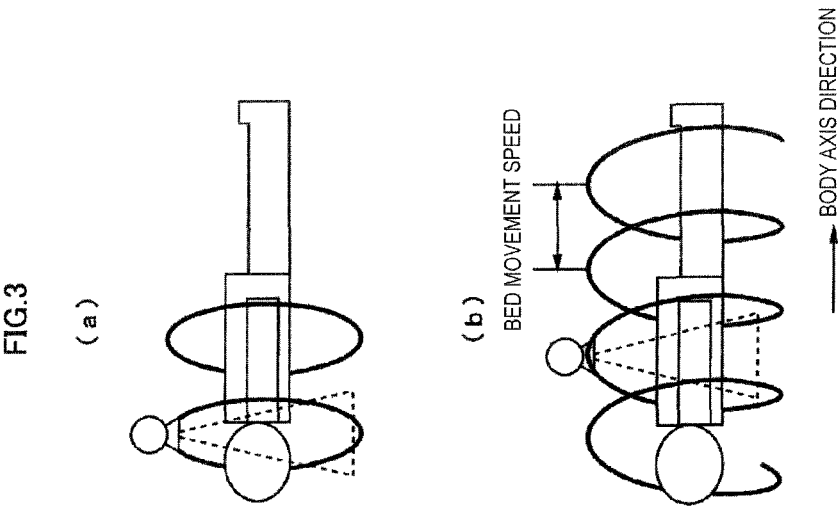
FIG. 3 is a diagram illustrating an axial scan and a spiral scan.

As shown in FIG. 2, the X-ray CT apparatus 1 is configured to mainly include the scanner 2, an operating unit 3, and the bed 4.

The scanner 2 is configured to include the X-ray tube 11 (X-ray generator), the detector 12, a collimator 13, a driving device 14, a central controller 15, an X-ray controller 16, a high voltage generator 17, a scanner controller 18, a bed controller 19, a bed movement measuring device 20, a collimator controller 21, a preamplifier 22, and an A/D converter 23.

The central controller 15 receives an input of scanning conditions or reconstruction parameters from the input device 6 in the operating unit 3, and transmits control signals required for scanning to the collimator controller 21, the X-ray controller 16, the scanner controller 18, and the bed controller 19.

The collimator controller 21 controls the position of the collimator 13 on the basis of the control signal.

When a scanning is started in response to the scanning start signal, the X-ray controller 16 controls the high voltage generator 17 on the basis of the control signal. The high voltage generator 17 applies a tube voltage and a tube current to the X-ray tube 11 (X-ray generator). In the X-ray tube 11, electrons of energy corresponding to the applied tube voltage are emitted from the cathode, and the emitted electrons collide with a target (anode). As a result, the object 10 is irradiated with X-rays of energy corresponding to the electron energy.

In addition, the scanner controller 18 controls the driving device 14 on the basis of the control signal. The driving device 14 rotates a gantry unit, in which the X-ray tube 11, the detector 12, the preamplifier 22, and the like are mounted, around the object 10.

The bed controller 19 controls the bed 4 on the basis of the control signal.

X-rays emitted from the X-ray tube 11 are absorbed (attenuated) into each tissue in the object 10 according to the X-ray attenuation coefficient after the irradiation region is restricted by the collimator 13, and the X-rays are transmitted through the object 10 and detected by the detector 12 disposed at the position facing the X-ray tube 11. The detector 12 is formed by a plurality of detection elements disposed in a two-dimensional direction (a channel direction and a row direction perpendicular to the channel direction). X-rays received by each detection element are converted into projection data (hereinafter, referred to as "actual projection data"). That is, X-rays detected by the detector 12 are converted into a current, amplified by the preamplifier 22, converted into digital data by the A/D converter 23, subject to LOG conversion and calibration, and input to the computation device 5 as actual projection data.

At this time, the X-ray tube 11 and the detector 12 facing each other rotate around the object 10. Accordingly, actual projection data is collected at the discrete X-ray tube positions (and corresponding detector positions) in the rotational direction. The acquisition unit of actual projection data at each X-ray tube position is called a "view".

The computation device 5 is configured to include a reconstruction computation unit 31, an image processing unit 32, and the like. In addition, an input/output device 9 is configured to include the input device 6, the display device 7, a storage device 8 (storage unit), and the like.

The reconstruction computation unit 31 generates a reconstructed image by performing image reconstruction processing using the actual projection data. The reconstruction computation unit 31 forms a tomographic image in a non-destructive manner as a distribution map of the X-ray attenuation coefficient of the inside of the object 10 by generating filter correction projection data by overlapping a reconstruction filter on the actual projection data of each view and performing back projection processing by applying a weight in a view direction (hereinafter, referred to as a "view-direction weight") for the filter correction projection data.

The reconstruction computation unit 31 stores the generated reconstructed image in the storage device 8. In addition, the reconstruction computation unit 31 displays the reconstructed image on the display device 7 as a CT image. Alternatively, the image processing unit 32 performs image processing on the reconstructed image stored in the storage device 8, and displays the image-processed reconstructed image on the display device 7 as a CT image.

Types of the X-ray CT apparatus 1 are largely divided into a multi-slice CT, which uses the detector 12 in which detection elements are arrayed in a two-dimensional direction, and a single-slice CT, which uses the detector 12 in which detection elements are arrayed in a row, that is, in a one-dimensional direction (only in a channel direction). In the multi-slice CT, X-ray beams spreading in a conical shape or in a pyramid shape are irradiated from the X-ray tube 11, which is an X-ray source, according to the detector 12. In the single-slice CT, X-ray beams spreading in a fan shape are irradiated from the X-ray tube 11. Typically, in the scanning of the X-ray CT apparatus 1, X-rays are irradiated while the gantry unit is rotating around the object 10 placed on the bed 4 (however, except for scanogram imaging).

As shown in FIG. 3(a), a scanning in which the bed 4 is fixed and the X-ray tube 11 rotates around the object 10 in the shape of circular orbit is called an axial scan or the like. In addition, as shown in FIG. 3(b), a scanning in which the bed 4 moves and the X-ray tube 11 rotates around the object 10 in the shape of spiral orbit is called a spiral scan or the like.

In the case of an axial scan, the bed controller 20 maintains the bed 4 in a stationary state. In addition, in the case of a spiral scan, the bed controller 20 performs parallel movement of the bed 4 in a body axis direction according to the bed movement speed as the scanning conditions input through the input device 6.

The X-ray CT apparatus 1 according to the embodiment of the present invention is a multi-slice CT, for example. In addition, the scanning method of the X-ray CT apparatus 1 is a rotate-rotate method (third generation), for example.

Figure 4:
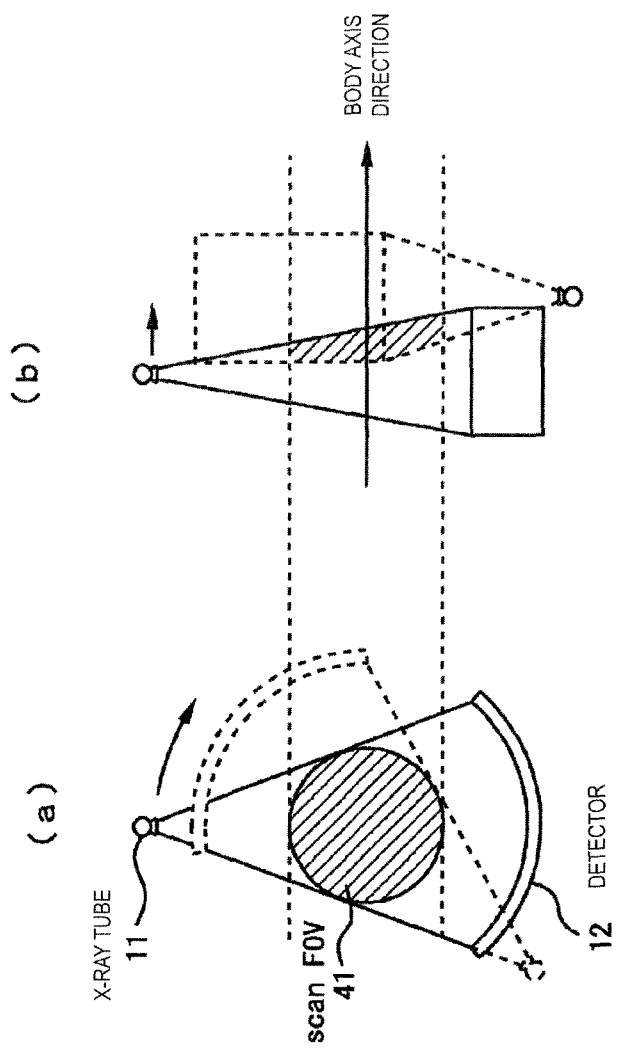
FIG. 4 is a diagram illustrating a scanFOV 41.

Next, image reconstruction processing, which is a prerequisite for each embodiment, will be described with reference to FIGS. 4 and 5. Specifically, (1) an iterative approximation method using a penalized weighted least-square error function as an evaluation function and (2) an iterative approximation method of performing view-direction weighted back projection processing will be described.

First, the iterative approximation method using the penalized weighted least-square error function as an evaluation function will be described. This has been proposed in NPL 1, for example, and the update expression is expressed as in the following expression.

$$x^{(k+1)} = x^{(k)} + S[A^T D(y - Ax^{(k)}) + \beta R x^{(k)}] \tag{1}$$

Here, $X^{(k)}$ is a vector (image vector) indicating an image in the k-th iterative update, and y is a vector indicating actual projection data. A is a matrix that maps an image and projection data, and is called a system matrix since this expresses the characteristics of a scanning system through the above-described mathematical model. $A^T$ indicates a transposed matrix of A.

$Ax^{(k)}$ is equivalent to processing (forward projection processing) to convert the image vector $X^{(k)}$ into a projection data vector. In addition, $A^T(.)$ is equivalent to processing (back projection processing) to convert the projection data vector in parentheses into an image vector.

D is a diagonal matrix having a weight coefficient, which is weighted to the difference value between the actual projection data and the forward projection data, as a diagonal element. In the image reconstruction of CT, a value corresponding to the number of detected photons is assumed to be the weight coefficient.

β is an arbitrary parameter that adjusts the strength of a penalty term. The penalty term serves to suppress the high frequency enhancement effect of the image by application of the iterative approximation method.

S is a matrix having an inverse of each element of a vector s, which is expressed by the following expression, as a diagonal element.

$$s = (A^T D A + \beta R')c \tag{2}$$

Here, c is a vector that has the number of elements equal to that of the image vector and that has 1 as values of all elements. R in expression (1) and R' in expression (2) are linear operators of the first derivative and the second derivative of the penalty term, and both are transformation matrices from an image vector to an image vector.

Elements of m row and n column of R and R' are expressed as in the following expressions, respectively.

$$R = \begin{cases} -l_{mn} + \sum_{j=1}^{J} l_{mj} & (m = n) \\ -l_{mn} & (m \neq n) \end{cases} \tag{3}$$

$$R' = \begin{cases} -l_{mn} + \sum_{j=1}^{J} l_{mj} & (m = n) \\ 0 & (m \neq n) \end{cases} \tag{4}$$

Here, $l_{mn}$ is an inverse of the distance between the m-th pixel and the n-th pixel. In addition, in the above explanation, the case where the quadratic function is used as a penalty term is shown as an example.

In the update expression shown in expression (1), matrices that are transposed matrices of each other in forward projection processing and back projection processing are applied.

Next, the iterative approximation method of performing view-direction weighted back projection processing will be described. This has been proposed in NFL 2, for example. In addition, the view-direction weighted back projection processing itself has been proposed in NPL 3.

Assuming that the back projection matrix corresponding to the view-direction weighted back projection processing is $B^T(.)$, the method proposed in NPL 2 is expressed as in the following expression.

$$x^{(k+1)} = x^{(k)} + \alpha B^T(y - Ax^{(k)}) + \alpha \beta R x^{(k)} \tag{5}$$

α is a relaxation coefficient related to the speed and stability of convergence in the iterative approximation method. When matrices that are not transposed matrices of each other in forward projection processing and back projection processing are applied (in the case of A≠B), it is necessary to set the relaxation coefficient in the range of a specific value for stable convergence in the iterative approximation method.

In order to describe this, expression (5) is first modified as follows.

$$x^{(k+1)} = Q x^{(k)} + \alpha B^T y \tag{6}$$

$$Q = I - \alpha B^T A + \alpha \beta R \tag{7}$$

In the embodiment of the present invention, a matrix Q in expression (7) is called an update matrix. The update matrix is a matrix to determine an update amount and an update direction of an image per one iterative update processing on the basis of update expression. I indicates a unit matrix.

Assuming that the spectral radius of the update matrix is ρ(Q), it is known that an image vector $x^{(k+1)}$ in expression (6) converges on expression (9) shown below under the conditions of expression (8) shown below. In addition, the spectral radius of the matrix is a least upper bound of the absolute value of the eigenvalue of the matrix.

$$\rho(Q) < 1 \tag{8}$$

$$\lim_{k \to \infty} x^{(k)} = (B^T A - \beta R)^{-1} \alpha B^T y \tag{9}$$

Here, $(.)^{-1}$ indicates an inverse matrix of the matrix in parentheses.

By setting the relaxation coefficient α such that the update matrix of expression (7) satisfies the conditions of expression (8), convergence in the iterative approximation method becomes stable.

In addition, in the method proposed in NPL 4, the spectral radius p (Q) shown in expression (8) is calculated and the relaxation coefficient α is set by calculating the maximum eigenvalue of the update matrix using the power law. However, the power law is not a method for solving the problem analytically, and computation time is increased since it is necessary to compute the large matrix operations sequentially.

Meanwhile, generally, when a spiral scan is performed at high bed movement speed, actual projection data in a row direction is insufficient. Accordingly, there is a problem in that the region where an image is obtained by the iterative approximation method is restricted.

This problem will be described with reference to FIGS. 4 and 5.

FIG. 4(a) shows the arrangement of the X-ray tube 11 and the detector 12 on the scanning cross-section. In addition, FIG. 4(a) shows a scanFOV 41 on the scanning cross-section. The scanFOV 41 is a region where an image is formed on the basis of the projection cutting plane theorem. The scanFOV 41 on the scanning cross-section is almost circular.

FIG. 4(b) shows the arrangement of the X-ray tube 11 and the detector 12 in the body axis direction. In addition, FIG. 4(b) shows the scanFOV 41 in the body axis direction. The scanFOV 41 in the body axis direction is a polygon, such as a triangle, a rectangle, or a pentagon, even though it changes with the bed movement speed.

Figure 5:
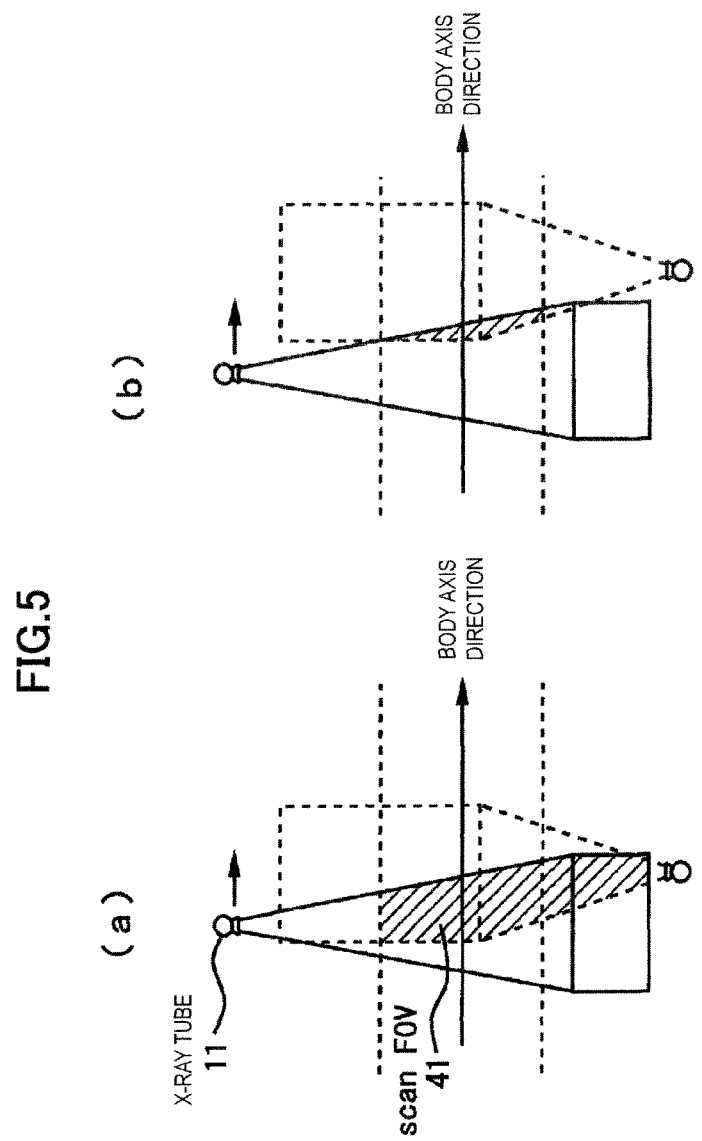
FIG. 5 is a diagram illustrating a difference in the scanFOV 41 due to a difference in the bed movement speed.

FIG. 5 shows a difference in the scanFOV 41 in the body axis direction due to the difference in the bed movement speed. When FIGS. 5(a) and 5(b) are compared with each other, it can be seen that the width of the scanFOV 41 in the body axis direction decreases as the bed movement speed increases. When the width of the scanFOV 41 in the body axis direction is smaller than a predetermined value, this means that a view of 180° required to reconstruct a certain tomographic image cannot be acquired and therefore a region where an image can be generated is restricted.

For the same reason, also in the peripheral field of view in the body axis direction at the time of an axial scan, the region where an image can be generated is restricted.

In addition, also within the scanning cross-section, it is similarly restricted when the object 10 protrudes in a channel direction of the detector 12.

Hereinafter, embodiments of the present invention will be specifically described on the assumption of those described above.

First Embodiment

In a first embodiment, the value of the relaxation coefficient for stable convergence in an iterative approximation method is analytically calculated before performing image reconstruction processing. Then, image reconstruction processing based on the iterative approximation method to perform view-direction weighted back projection processing is executed.

In the view-direction weighted back projection processing, the characteristics of a scan of the X-ray CT apparatus 1 shown below are used.

(1) As shown in FIG. 6, for views with different scanning phases by half a rotation (180° in the rotational direction), corresponding channels and rows of which transmission paths of X-rays approximately overlap each other are present, and actual projection data thereof are highly correlated with each other. FIG. 6(a) shows a transmission path of an observed view and a transmission path of an opposite phase view in the channel direction. FIG. 6(b) shows a transmission path of an observed view and a transmission path of an opposite phase view in the row direction. Hereinafter, data satisfying such a relationship will be called actual projection data of opposite phases.

(2) As described above, in the X-ray CT apparatus 1, a scanning time difference occurs in the view direction of actual projection data since the data is collected while rotating the X-ray tube 11 and the detector 12. If the bed movement speed is constant during the scanning, the scanning time difference is proportional to the distance between the position of the X-ray tube 11 in the body axis direction and the position of the image in the body axis direction.

Figure 7:
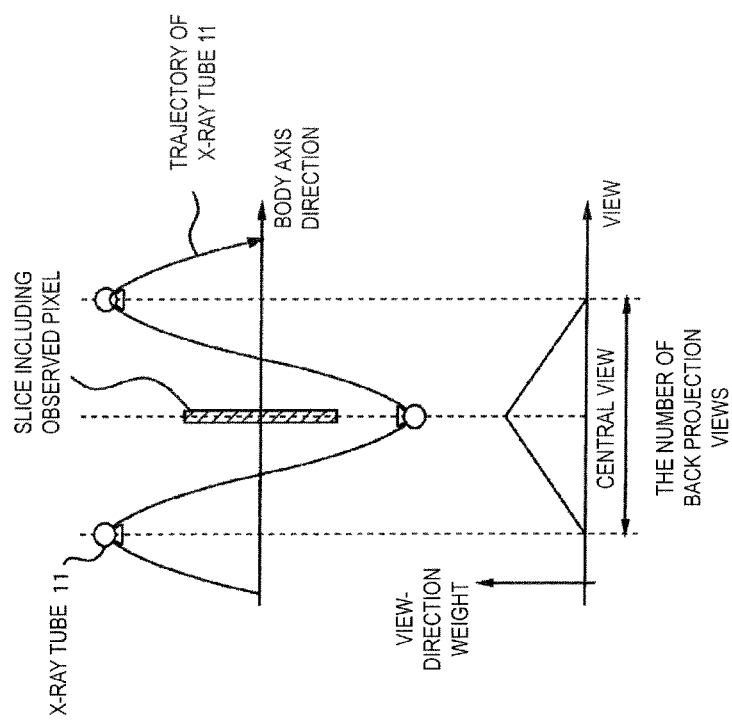
FIG. 7 is a diagram illustrating a view-direction weight.

FIG. 7 is a conceptual diagram of the view-direction weight. As shown in FIG. 7, the computation device 5 of the X-ray CT apparatus 1 adds, as the view-direction weight, a weight so as to become 1 when added between actual projection data of opposite phases according to the distance between the position of a slice, which includes an observed pixel, in the body axis direction and the position of the X-ray tube 11 in the body axis direction. In addition, the computation device 5 of the X-ray CT apparatus 1 applies the weight of 0 excluding a predetermined number of views on both sides of a view of the position of the X-ray tube 11 in the body axis direction, which is closest to an observed pixel in the body axis direction, as a view-direction weight. Hereinafter, a view to which a weight, which is not 0, is given will be called a back projection view, and the number of back projection views will be called a back projection view number.

An appropriate value of the back projection view number is determined by the spiral pitch (value determined by the bed movement speed and the gantry rotation speed as scanning conditions) and the length of the detector 12 in the row direction.

By defining the view-direction weight in this manner, it is possible to improve the time resolution compared with a case where the view-direction weight is not used. This is because the time phases of multiple views contributing to image reconstruction processing are almost equal due to the view-direction weight.

Regarding the definition of the view-direction weight, it is possible to use a common back projection view number in all pixels and determine a central view for each slice, in the same manner as in the Feldkamp method. In addition, regarding the definition of the view-direction weight, it is also possible to determine a central view for each pixel as disclosed in "JP-A-2004-199163". In addition, regarding the definition of the view-direction weight, it is also possible to determine the back projection view number in each pixel.

Assuming that the index of a vector of actual projection data is i (i=1, . . . , I) and the index of an image vector is j (j=1, . . . , J), the view-direction weight is defined as $w_{ij}$ since it is set for each element of the vector of the actual projection data and the image vector. In the i-th projection data and the j-th pixel, assuming that an element of the system matrix A is $a_{ij}$ and an element of the system matrix B multiplied by the view-direction weight is $b_{ij}$, b is expressed as in the following expression.

$$b_{ij} = w_{ij} a_{ij} \qquad (10)$$

In this case, a back projection matrix indicating the view-direction weighted back projection processing is $B^T$. When the $B^T$ is used in the back projection processing of the iterative approximation method, convergence in the algorithm under the conditions of expression (8) occurs as described above.

Here, an example of calculating the system matrix A will be described.

As described above, the system matrix A is a matrix that maps an image and projection data.

The computation device 5 of the X-ray CT apparatus 1 calculates each element $a_{ij}$ on the basis of the apparatus specification of the X-ray CT apparatus 1 and the scanning conditions input through the input device 6. As an example of the method of calculating the system matrix A, a Joseph method proposed in "Joseph, P. M. (1982). An Improved Algorithm for Reprojecting Rays Through Pixel Images. IEEE Transactions on Medical Imaging MI-1, 192-196." may be mentioned.

As examples of the apparatus specification of the X-ray CT apparatus 1 used to calculate the system matrix A, the following may be mentioned.

The number of elements in a row direction in the detector 12

The number of elements in a channel direction in the detector 12

The size of one element in a row direction in the detector 12

The size of one element in a channel direction in the detector 12

Distance $d_{sod}$ between the X-ray tube 11 and the center of rotation

Distance $d_{sid}$ between the X-ray tube 11 and the center (detector center) of the detector 12

In addition, as examples of the scanning conditions used to calculate the system matrix A, the following may be mentioned. In addition, for unclear scanning conditions, the settings are illustrated.

Beam pitch (value obtained by dividing the bed movement speed by the row-direction detector size at the center of rotation): "value equivalent to high speed" or "value equivalent to low speed", and the like The number of rotations in scanning Angle at the start of scanning Rotation speed The number of scanning views per rotation Scanning method: "axial scan" or "spiral scan", or the like The number of pixels (within a cross-section): the number of pixels in a horizontal direction×the number of pixels in a vertical direction The number of image slices Pixel size (within a cross-section)

Image slice thickness

Image center position (within a cross-section): "matched with the center of rotation" or the like Center position in an image slice direction: "matched with the number of rotations in scanning of 2.5" or the like The number of dimensions I of the vector of the actual projection data described above is determined from the apparatus specification and the scanning conditions. Specifically, I is "the number of elements in a row direction in the detector 12×the number of elements in a channel direction in the detector 12×the number of scanning views per rotation×the number of rotations in scanning". Similarly, the number of dimensions J of the image vector is also determined from the scanning conditions. Specifically, J is "the number of pixels in a horizontal direction×the number of pixels in a vertical direction×the number of image slices".

For example, the system matrix A is different between the case where the beam pitch which is one of the scanning conditions is the "value equivalent to high speed" and the case where the beam pitch which is one of the scanning conditions is the "value equivalent to low speed". Therefore, the relaxation coefficient α for stable convergence in the iterative approximation method is also different.

In the above-described NPL 4, however, there is a problem in that the computation time and the amount of memory required for computation are large although the spectral radius of the update matrix is calculated using the power law. Therefore, in the X-ray CT apparatus 1 of the present invention, the operator norm of the update matrix is calculated instead of calculating the spectral radius of the update matrix.

Generally, the operator norm of a matrix has the following characteristics.

(1) An operator norm $\|C\|$ of a certain square matrix C when adopting the p-norm as a norm of a certain vector x is expressed as in the following expression.

$$\|C\| = \sup_{x \neq 0} \frac{\|Cx\|_p}{\|x\|_p} \quad (11)$$

(2) The following expression is satisfied for any operator norm $\|C\|$.

$$\rho(C) \leq \|C\| \quad (12)$$

Using the two characteristics described above, expression (8) can be replaced as the following expression.

$$\|Q\| < 1 \quad (13)$$

Apparently, when the operator norm of the update matrix is smaller than 1 (when expression (13) is satisfied), the spectral radius of the update matrix is smaller than 1 (expression (8) is satisfied).

Hereinafter, an example where the view-direction weighted back projection processing and the relaxation coefficient are introduced into the method proposed in NPL 3 will be shown. However, the present invention is not limited to this example, and can be applied to any iterative approximation method including an update matrix, in which the spectral radius can be adjusted using a relaxation coefficient, in the update expression.

First, the following expression is obtained by introducing the back projection matrix $B^T$ and the relaxation coefficient α of the view-direction weighted back projection processing into expression (1).

$$x^{(k+1)} = x^{(k)} + \alpha S[B^T D(y - Ax^{(k)}) + \beta R x^{(k)}] \quad (14)$$

Here, S is a matrix having an inverse of each element of a vector s, which is expressed by the following expression, as a diagonal element.

$$s = (B^T DA + \beta R')c \quad (15)$$

In addition, if the update matrix Q is derived in the same manner as in expression (7), the following expression is obtained.

$$Q = I - \alpha(SB^T DA + \beta SB) \quad (16)$$

The following expression is obtained by substituting expression (16) into expression (13).

$$\|I - \alpha(SB^T DA + \beta SR)\| < 1 \quad (17)$$

By determining the relaxation coefficient α such that expression (17) is satisfied, update expression shown in expression (14) is stably converged.

Here, the order of the operator norm of the matrix on the left side of expression (17) is arbitrary.

For example, when 1-norm (first-order norm) is adopted in expression (17), it is preferable that the computation device 5 of the X-ray CT apparatus 1 add elements of a matrix I-α (SB$^T$DA+βSR) in a row direction and set a maximum value in a row direction as the value of the operator norm $$\|I - \alpha(SB^T DA \alpha \beta SR)\|.$$

As described above, the computation device 5 of the X-ray CT apparatus 1 calculates the relaxation coefficient α analytically on the basis of the scanning conditions. In this manner, the X-ray CT apparatus 1 can determine the relaxation coefficient α quickly and easily compared with the iterative solution of the eigenvalue problem represented by the power law.

In addition, since the relaxation coefficient α is determined on the basis of scanning conditions, it is possible to ensure the stability of the algorithm compared with a case where the relaxation coefficient α is determined experientially.

Details of the relaxation coefficient calculation processing will be described with reference to FIG. 8.

When the scanner 2 acquires the actual projection data of the object 10 on the basis of the scanning conditions and the operator sends an instruction of image reconstruction through the input device 6, the computation device 5 of the X-ray CT apparatus 1 calculates matrices A, B, D, R, and R' in expression (17) on the basis of the scanning conditions input through the input device 6 (step 1).

Then, the computation device 5 calculates each element of the matrix $I-\alpha(SB^T DA+\beta SR)$ (step 2).

Then, the computation device 5 calculates the operator norm $\|I-\alpha(SB^T DA+\beta SR)\|$ of the matrix $I-\alpha(SB^T DA+\beta SR)$ (step 3).

Then, the computation device 5 determines the relaxation coefficient α such that expression (17) (predetermined conditional expression) is satisfied (step 4).

Thus, the computation device 5 of the X-ray CT apparatus 1 calculates the relaxation coefficient α analytically on the basis of the scanning conditions.

After the relaxation coefficient α is determined, the computation device 5 of the X-ray CT apparatus 1 reconstructs a tomographic image by performing iterative approximation on the actual projection data using the update expression of the iterative approximation method including the scanning conditions and the relaxation coefficient α. As described above, in the iterative approximation method in the first embodiment, matrices that are not transposed matrices of each other in forward projection processing and back projection processing are applied. In addition, the update expression of the iterative approximation method in the first embodiment is expression (14).

In the first embodiment, the relaxation coefficient is calculated such that expression (17) defined on the basis of the operator norm of the update matrix Q shown in expression (16) is satisfied. Accordingly, iterative update processing based on the update expression of expression (14) is stably converged.

Expression (17) is an expression showing that the operator norm of the update matrix Q is smaller than 1. Here, it is preferable that the computation device 5 of the X-ray CT apparatus 1 calculate the value of the relaxation coefficient α applied to expression (14) as a maximum value satisfying the conditional expression of expression (17). That is, it is preferable that the computation device 5 set the largest possible value within a range, which satisfies the conditional expression of expression (17), as the relaxation coefficient α applied to expression (14).

Accordingly, since the number of iterations of the iterative update processing is reduced, computation time is shortened and the quality of a reconstructed image is also improved.

In addition, in the iterative approximation method of the first embodiment, back projection processing using the view-direction weight is performed. The computation device 5 reconstructs a tomographic image of the object 10 by calculating a view-direction weight to apply the weight of 0 excluding a predetermined number of views on both sides of a view of the X-ray tube position closest to an observed pixel in the body axis direction, calculating the back projection matrix $B^T$ applied as back projection processing using the view-direction weight, and performing iterative approximation on the actual projection data using the update expression of expression (14) to which the back projection matrix $B^T$ is applied.

Therefore, it is possible to eliminate the redundancy of projection data and also to improve the time resolution. As a result, it is possible to suppress the degradation of image quality when the iterative approximation method is applied for the data including the body movement.

In the above explanation, when the scanner 2 acquires the actual projection data, the computation device 5 of the X-ray CT apparatus 1 calculates the relaxation coefficient α on the basis of the scanning conditions and performs iterative approximation on the actual projection data using the relaxation coefficient α calculated by itself.

In the present invention, however, the device that performs the processing of calculating the relaxation coefficient α is not limited to the computation device 5.

Figure 8:
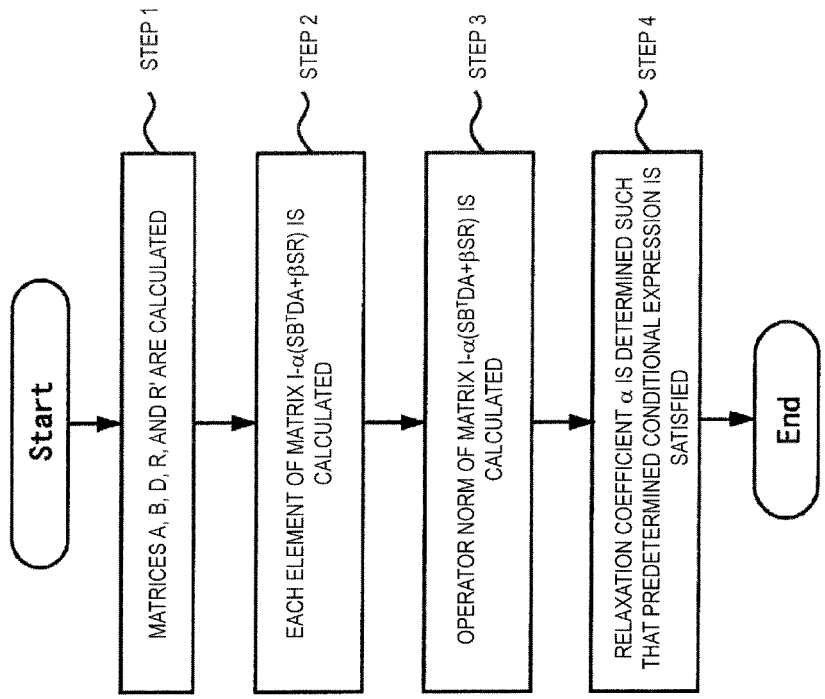
FIG. 8 is a flow chart showing the relaxation coefficient calculation process.

For example, the computation device 5 of the X-ray CT apparatus 1 or other computers perform the processing of calculating the relaxation coefficient α, which is shown in FIG. 8, for each of various scanning conditions (for example, scanning conditions used to calculate the system matrix A described above) and store the calculation result in the storage device 8 of the X-ray CT apparatus 1. That is, the storage device 8 stores the relaxation coefficient α for each of scanning conditions.

In addition, when the scanner 2 acquires the actual projection data, the computation device 5 of the X-ray CT apparatus 1 searches for the setting value of the relaxation coefficient α stored in the storage device 8 using the scanning condition input through the input device 6 as a search key and performs iterative approximation on the actual projection data using the setting value of the relaxation coefficient α acquired as the search result.

Second Embodiment

In a second embodiment, image reconstruction processing based on the iterative approximation method to perform data extension type back projection processing is executed using the relaxation coefficient α calculated analytically in the first embodiment.

Such image reconstruction processing is effective when it is necessary to image a range, which is long in the body axis direction of the object 10, in a predetermined time. For example, such image reconstruction processing is effective when shortening the scanning time takes priority over the quality of an image in a situation of a medical emergency. In the present invention, however, it is possible to maintain the quality of an image at a fixed level while realizing the shortening of the scanning time.

Figure 9:
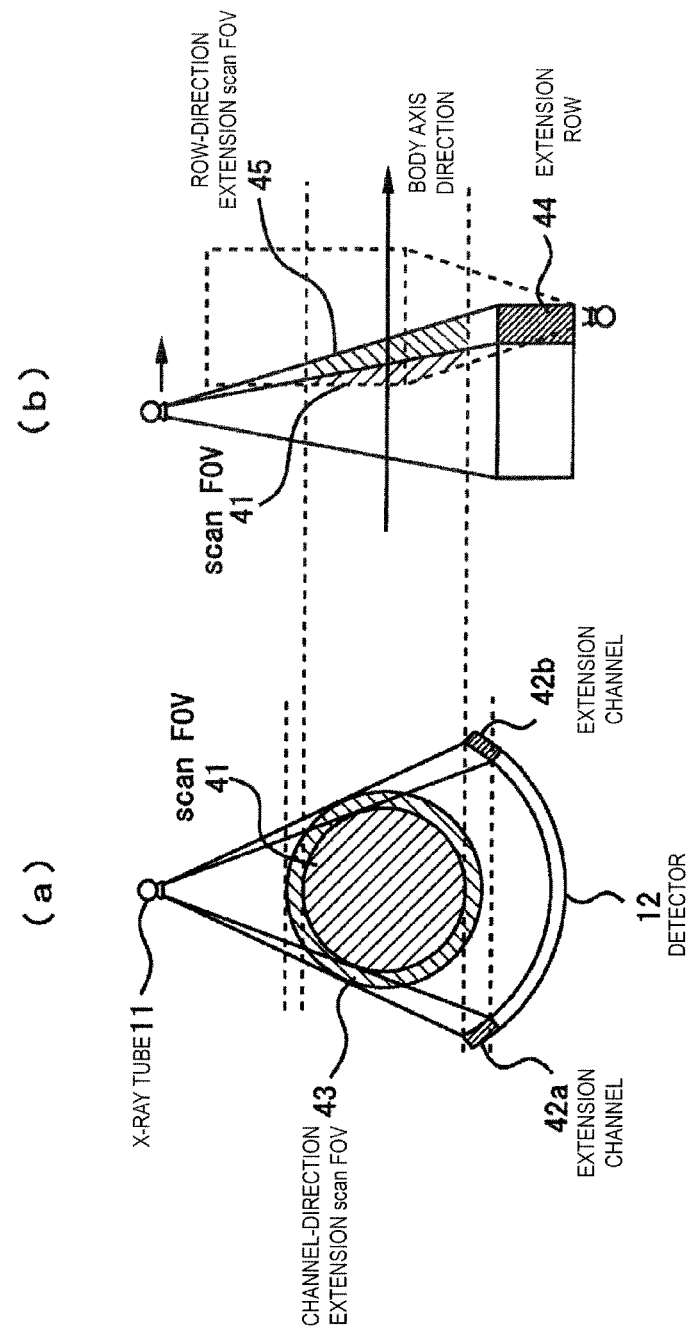
FIG. 9 is a diagram illustrating an extension scanFOV.

An object of the data extension type back projection processing is to extend projection data in the channel and row directions and expand the scanFOV 41 using the virtual projection data (hereinafter, referred to as "extended projection data"), as shown in FIG. 9. The scanFOV 41 extended by applying the data extension type back projection processing will be called "extension scanFOV" hereinbelow.

FIG. 9(*a*) shows an extension in the channel direction. Extension channels 42a and 42b are projection data extended in the channel direction. In addition, a channel-direction extension scanFOV 43 is obtained by extending the scanFOV 41 by application of the data extension type back projection processing using the extension channels 42a and 42b.

FIG. 9(*b*) shows an extension in the row direction. An extension row 44 is projection data extended in the row direction. In addition, a row-direction extension scanFOV 45 is obtained by extending the scanFOV 41 by application of the data extension type back projection processing using the extension row 44.

Details of the data extension type back projection processing will be described with reference to FIG. 10.

Figure 10:
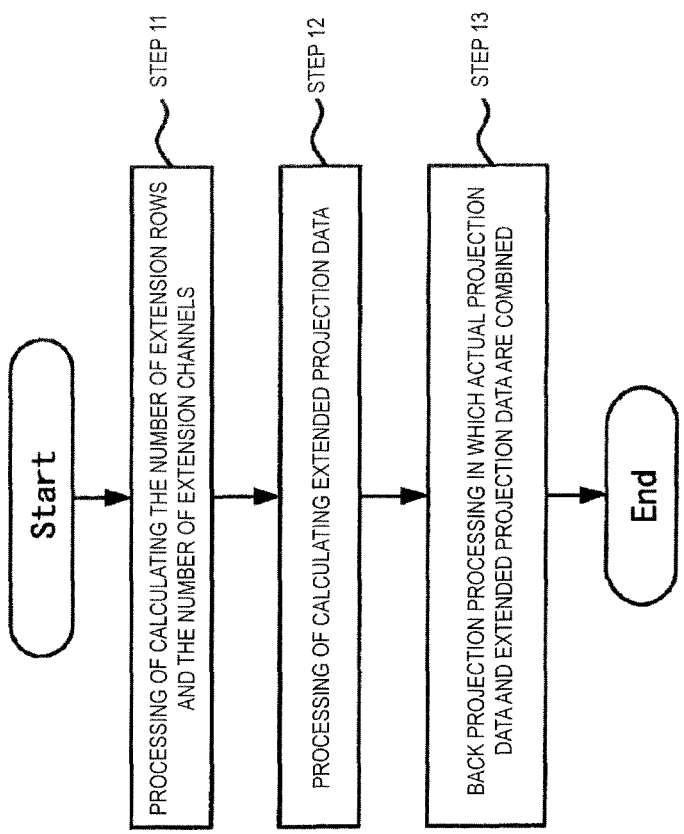
FIG. 10 is a flow chart showing data extension type back projection processing.

As shown in FIG. 10, the computation device 5 of the X-ray CT apparatus 1 performs the processing of calculating the number of extension rows and the number of extension channels on the basis of the scanning conditions input through the input device 6 (step 11).

An example where the computation device 5 calculates the number of extension rows will be described with reference to FIGS. 11 and 12. However, the present invention is not limited to this example, and the operator may set the number of extension rows arbitrarily. In addition, in the case of an axial scan, the processing of calculating the number of extension rows may be performed in the same manner as in PTL 1, for example.

Figure 11:
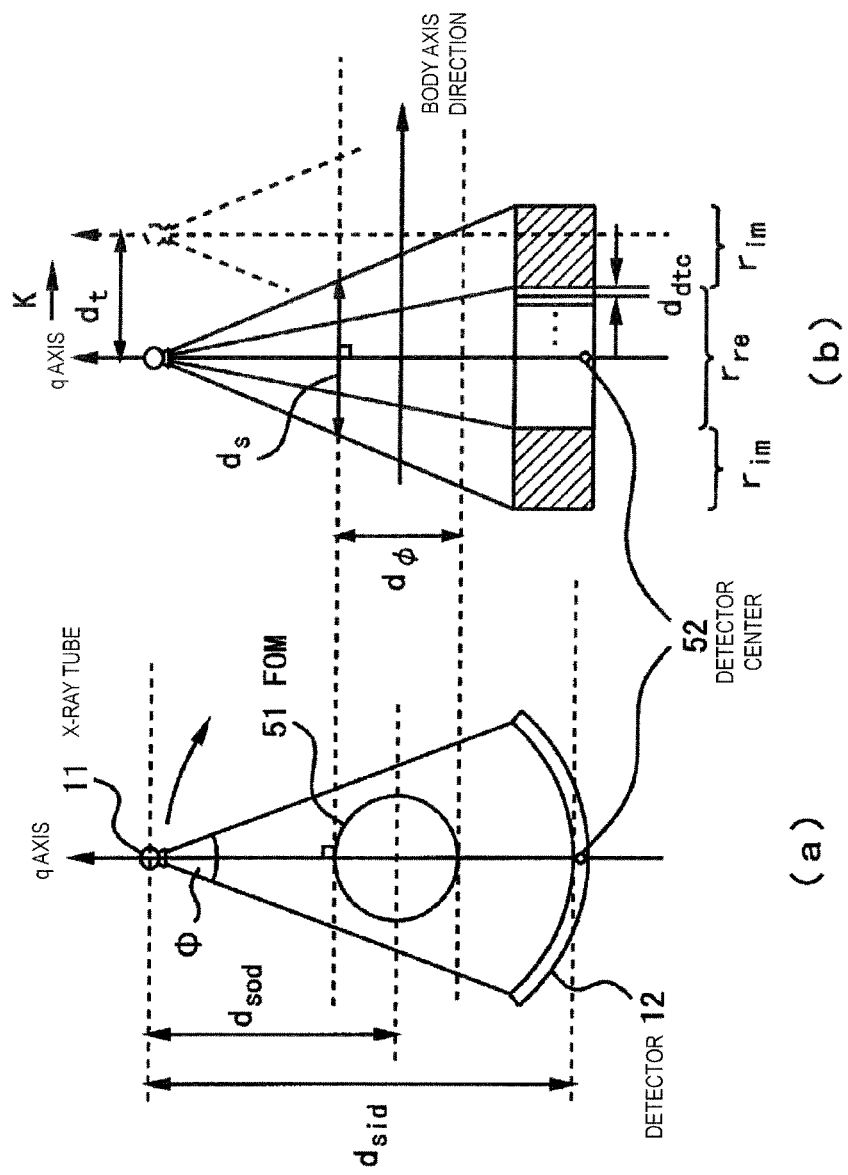
FIG. 11 is a diagram illustrating the processing of calculating the number of extension rows.

As shown in FIG. 11, a distance between the X-ray tube 11 and the center of rotation is set to $d_{sod}$. In addition, a distance between the X-ray tube 11 and the center (detector center 52) of the detector 12 is set to $d_{sid}$. In addition, an FOM size which is the size of FOM (Field Of Measurement) 51 is set to $d_\phi$.

Figure 12:
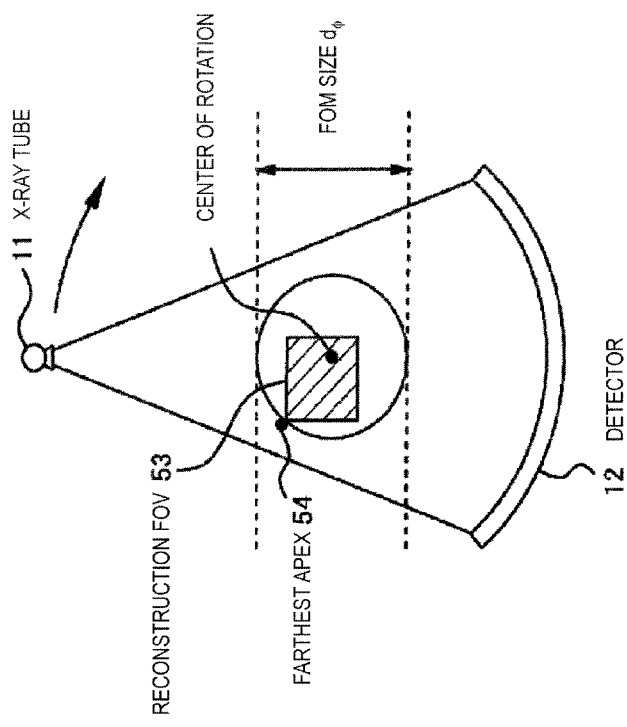
FIG. 12 is a diagram illustrating the FOM size.

Here, the FOM size $d_\phi$ is twice the distance between the center of rotation and an apex 54, which is farthest from the center of rotation, among the apices of a reconstruction FOV 53 (image region to be generated), as shown in FIG. 12.

In addition, it is assumed that the opening width of a detection element in the body axis direction is $d_{dtc}$, the number of rows of a detection element is $r_{re}$, and the number of extended rows is $r_{im}$. A straight line connecting the X-ray tube 11 and the detector center 52 is set to the q axis. Since the length of a row of detection elements is constant, the number of extension rows is determined by calculating $r_{im}$.

Here, a plane close to the X-ray tube 11 (hereinafter, referred to as "X-ray tube side plane") between two planes, which are perpendicular to the q axis and are in contact with an FOM 51, is focused. Assuming that the crossing length of the X-ray tube side plane and an X-ray beam in the body axis direction is $d_s$, $d_s$ is expressed as in the following expression.

$$d_s = \frac{d_{dtc}(r_{re} + r_{im})\{d_{sod} - (d_\phi/2)\}}{d_{sid}} \quad (18)$$

In addition, assuming that the fan angle is $\phi$ and the bed movement speed is $\kappa$ (unit is a movement distance per one rotation [mm/rot], for example), when the observation system has rotated by $\pi+\phi$ [rad], the relative movement amount $d_t$ of the observation system with respect to the bed 4 in the body axis direction is expressed as in the following expression.

$$d_t = \kappa[F + \{\phi/(2\pi)\}] \quad (19)$$

Here, F is a back projection phase width. In the present embodiment, F is a parameter for adjusting trade-offs between the degradation of image quality due to estimation error of extended projection data and the degradation of image quality due to the loss of actual projection data.

When $d_s$ in expression (18) and $d_t$ in expression (19) are equal, scanning conditions with no data loss are obtained since FOM 51 is included inside the scanFOV 41. Then, $r_{im}$ is calculated according to the following expression.

$$r_{im} = \frac{d_{sid}\kappa[F + \{\Phi/(2\pi)\}]}{d_{dtc}\{d_{sod} - (d_\phi/2)\}} - r_{re} \quad (20)$$

The computation device 5 of the X-ray CT apparatus 1 calculates the number of extended rows $r_{im}$ according to expression (20).

In addition, in the channel direction, it is preferable that the computation device 5 extend a channel so as to contain the extension scanFOV 43 within the scanning cross-section. In this case, the number of extension channels can be easily calculated.

Explanation continues referring back to FIG. 10.

Then, the computation device 5 performs processing of generating the extended projection data on the basis of the number of extension rows and the number of extension channels calculated in step 11 (step 12).

The processing of generating the extended projection data in step 12 will be described.

For the extension row calculated on the basis of expression (20), the index is set to r (r=1, . . . , $r_{im}$). In addition, the projection value of extended projection data is set to $\psi$ ($\psi_r$: r=1, . . . , $r_{im}$).

In the present embodiment, extended projection data in the row direction is estimated by extrapolation from the difference data between forward projection data and actual projection data. Here, as a simplest case, extended projection data in the row direction is estimated by zero-order extrapolation using data, which is located on the outermost side in the row direction, of data obtained as actual projection data.

Assuming that the transformation matrix from the actual projection data to the extended projection data is P ($p_{ri}$: r=1, . . . , $r_{im}$, i=1, . . . , I), the projection value y of the extended projection data is expressed as in the following expression.

$$\psi = P(y - Ax) \quad (21)$$

The computation device 5 of the X-ray CT apparatus calculates the projection value $\psi$ of the extended projection data according to expression (21).

Then, the computation device 5 performs back projection processing by combining the actual projection data of the object 10 acquired by the scanner 2 and the extended projection data generated in step 12 (step 13).

The back projection processing, in which the actual projection data and the extended projection data are combined in step 13, will be described.

A back projection matrix defined by y calculated in step 12 is set to Z ($z_{jr}$: j=1, . . . , J, r=1, . . . , $r_{im}$). Therefore, back projection processing of extended projection data is expressed as ZP(.).

In addition, back projection processing of actual projection data is expressed as $A^T$(.).

Therefore, assuming that an extended back projection matrix, which indicates back projection processing in which the actual projection data and the extended projection data are combined, is $B^T$, $B^T$ is expressed as in the following expression.

$$B^T = (A^T + ZP) \quad (22)$$

From the above, the iterative approximation method of performing data extension type back projection processing can be formulized by substituting expression (22) into expression (14).

Although the applications to the spiral scan have been described in the above, the present invention may also be applied to an axial scan. In addition, although the projection data has been extended in the channel and row directions, the projection data may also be extended in only one of the channel and row directions.

In the iterative approximation method in the second embodiment, the back projection processing is performed using the extended projection data obtained by extending the actual projection data in the channel direction and/or the row direction.

The computation device 5 of the X-ray CT apparatus 1 calculates the relaxation coefficient α analytically on the basis of the scanning conditions input through the input device 6, as in the first embodiment. In addition, the computation device 5 reconstructs a tomographic image by calculating the transformation matrix P from the actual projection data to the extended projection data on the basis of the scanning conditions input through the input device 6, calculating the extended back projection matrix $B^T (=A^T+ZP)$, which is applied as back projection processing in which the actual projection data and the extended projection data are combined, using the transformation matrix P, and performing iterative approximation on the actual projection data and the extended projection data using expression (14), to which the extended back projection matrix $B^T$ is applied, as update expression.

In this manner, it is possible to suppress the degradation of image quality when the iterative approximation method is applied under the scanning conditions in which data loss occurs at the time of an axial scan or a spiral scan of high bed movement speed.

In addition, it is also possible to combine the first and second embodiments.

In an iterative approximation method based on the combination of the first and second embodiments, back projection processing is performed using the extended projection data, which is obtained by extending the actual projection data in the channel direction and/or the row direction, and the view-direction weight.

First, the computation device 5 of the X-ray CT apparatus 1 calculates the relaxation coefficient α analytically on the basis of the scanning conditions input through the input device 6, as in the first embodiment.

Then, the computation device 5 calculates the transformation matrix P from the actual projection data to the extended projection data on the basis of the scanning conditions input through the input device 6. In addition, the computation device 5 calculates a view-direction weight to apply the weight of 0 excluding a predetermined number of views on both sides of a view of the X-ray tube position closest to an observed pixel in the body axis direction, and calculates the back projection matrix $B^T$ applied as back projection processing using the view-direction weight.

Then, the computation device 5 reconstructs a tomographic image by calculating an extended back projection matrix, which is applied as back projection processing in which the actual projection data and the extended projection data are combined, using the transformation matrix P and the view-direction weight and performing iterative approximation on the actual projection data and the extended projection data using the update expression of expression (14) to which the extended back projection matrix is applied.

Therefore, it is possible to eliminate the redundancy of projection data and also to improve the time resolution.

As a result, it is possible to suppress the degradation of image quality when the iterative approximation method is applied for the data including the body movement.

In addition, at the time of an axial scan or a spiral scan at the high bed movement speed, it is possible to suppress the degradation of image quality when the iterative approximation method is applied under the scanning conditions in which data loss occurs.

As described above, from the explanation regarding the various embodiments of the present invention, it is apparent that the object of the present invention is achieved. While the present invention has been described and shown in the drawings in detail, these are intended only for explanation and illustration, and the present invention is not limited to these. In addition, the subject matter of the present invent on limited by only the appended claims.

REFERENCE SIGNS LIST

1: X-ray CT apparatus
2: scanner
3: operating unit
4: bed
5: computation device
6: input device
7: display device
8: storage device
10: object
11: X-ray tube
12: detector
41: scanFOV
42a, 42b: extension channel
43: channel-direction extension scanFOV
44: extension row
45: row-direction extension scanFOV
51: FOM
52: detector center
53: reconstruction FOV

The invention claimed is:

1. An X-ray CT apparatus that reconstructs a tomographic image of an object using an iterative approximation method to apply matrices that are not transposed matrices of each other in forward projection processing and back projection processing, the apparatus comprising:
   a scanning unit that acquires actual projection data of the object on the basis of scanning conditions; and
   a computation unit that reconstructs the tomographic image by performing iterative approximation on the actual projection data using the scanning conditions and an update expression of the iterative approximation method including a relaxation coefficient that determines convergence of computation,
   wherein the relaxation coefficient is analytically calculated on the basis of the scanning conditions, and
   wherein the relaxation coefficient is calculated such that a predetermined conditional expression, which is defined on the basis of an operator norm of an update matrix that determines an update amount and an update direction of the update expression, is satisfied.

2. The X-ray CT apparatus according to claim 1, wherein the predetermined conditional expression is an expression showing that the operator norm of the update matrix is smaller than 1.

3. The X-ray CT apparatus according to claim 2, wherein the relaxation coefficient is calculated as a maximum value satisfying the predetermined conditional expression.

4. An X-ray CT apparatus that reconstructs a tomographic image of an object using an iterative approximation method to apply matrices that are not transposed matrices of each other in forward projection processing and back projection processing, the apparatus comprising:

a scanning unit that acquires actual projection data of the object on the basis of scanning conditions; and a computation unit that reconstructs the tomographic image by performing iterative approximation on the actual projection data using the scanning conditions and an update expression of the iterative approximation method including a relaxation coefficient that determines convergence of computation, wherein the relaxation coefficient is analytically calculated on the basis of the scanning conditions, and wherein, in the iterative approximation method, the back projection processing is performed using extended projection data obtained by extending the actual projection data in a channel direction and/or a row direction, and the computation unit reconstructs the tomographic image by calculating a transformation matrix from the actual projection data to the extended projection data on the basis of the scanning conditions, calculating an extended back projection matrix, which is applied as back projection processing in which the actual projection data and the extended projection data are combined, using the transformation matrix, and performing iterative approximation on the actual projection data and the extended projection data using the update expression to which the extended back projection matrix is applied.

5. An X-ray CT apparatus that reconstructs a tomographic image of an object using an iterative approximation method to apply matrices that are not transposed matrices of each other in forward projection processing and back projection processing, the apparatus comprising:

a scanning unit that acquires actual projection data of the object on the basis of scanning conditions; and a computation unit that reconstructs the tomographic image by performing iterative approximation on the actual projection data using the scanning conditions and an update expression of the iterative approximation method including a relaxation coefficient that determines convergence of computation, wherein the relaxation coefficient is analytically calculated on the basis of the scanning conditions, and wherein, in the iterative approximation method, back projection processing using a view-direction weight is performed, and the computation unit reconstructs the tomographic image by calculating the view-direction weight to apply a weight of 0 excluding a predetermined number of views on both sides of a view of an X-ray tube position closest to an observed pixel in a body axis direction, calculating a back projection matrix applied as the back projection processing using the view-direction weight, and performing iterative approximation on the actual projection data using the update expression to which the back projection matrix is applied.

6. An X-ray CT apparatus that reconstructs a tomographic image of an object using an iterative approximation method to apply matrices that are not transposed matrices of each other in forward projection processing and back projection processing, the apparatus comprising:

a scanning unit that acquires actual projection data of the object on the basis of scanning conditions; and a computation unit that reconstructs the tomographic image by performing iterative approximation on the actual projection data using the scanning conditions and an update expression of the iterative approximation method including a relaxation coefficient that determines convergence of computation, wherein the relaxation coefficient is analytically calculated on the basis of the scanning conditions, and wherein, in the iterative approximation method, the back projection processing is performed using extended projection data obtained by extending the actual projection data in a channel direction and/or a row direction and a view-direction weight, and the computation unit reconstructs the tomographic image by calculating a transformation matrix from the actual projection data to the extended projection data on the basis of the scanning conditions, calculating the view-direction weight to apply a weight of 0 excluding a predetermined number of views on both sides of a view of an X-ray tube position closest to an observed pixel in a body axis direction, calculating an extended back projection matrix, which is applied as back projection processing in which the actual projection data and the extended projection data are combined, using the transformation matrix and the view-direction weight, and performing iterative approximation on the actual projection data and the extended projection data using the update expression to which the extended back projection matrix is applied.

7. The X-ray CT apparatus according to claim 1, wherein, when the scanning unit acquires the actual projection data, the computation unit calculates the relaxation coefficient on the basis of the scanning conditions and performs iterative approximation on the actual projection data using the relaxation coefficient calculated by itself.

8. The X-ray CT apparatus according to claim 1, further comprising:

a storage unit that stores the relaxation coefficient for each of the scanning conditions, wherein, when the scanning unit acquires the actual projection data, the computation unit searches for the relaxation coefficient stored in the storage unit on the basis of the scanning conditions and performs iterative approximation on the actual projection data using the searched relaxation coefficient.

9. An image reconstruction method of reconstructing a tomographic image of an object using an iterative approximation method to apply matrices that are not transposed matrices of each other in forward projection processing and back projection processing, the method comprising:

a step of acquiring actual projection data of the object on the basis of scanning conditions; and a step of reconstructing the tomographic image by performing iterative approximation on the actual projection data using the scanning conditions and an update expression of the iterative approximation method including a relaxation coefficient that determines convergence of computation, wherein the relaxation coefficient is analytically calculated on the basis of the scanning conditions, and wherein the relaxation coefficient is calculated such that a predetermined conditional expression, which is defined on the basis of an operator norm of an update matrix that determines an update amount and an update direction of the update expression, is satisfied.

10. An image reconstruction method of reconstructing a tomographic image of an object using an iterative approximation method to apply matrices that are not transposed matrices of each other in forward projection processing and back projection processing, the method comprising:

a step of acquiring actual projection data of the object on the basis of scanning conditions; and a step of reconstructing the tomographic image by performing iterative approximation on the actual projection data using the scanning conditions and an update expression of the iterative approximation method including a relaxation coefficient that determines convergence of computation, wherein the relaxation coefficient is analytically calculated on the basis of the scanning conditions, and wherein, in the iterative approximation method, the back projection processing is performed using extended projection data obtained by extending the actual projection data in a channel direction and/or a row direction, and reconstruction of the tomographic image is performed by calculating a transformation matrix from the actual projection data to the extended projection data on the basis of the scanning conditions, calculating an extended back projection matrix, which is applied as back projection processing in which the actual projection data and the extended projection data are combined, using the transformation matrix, and performing iterative approximation on the actual projection data and the extended projection data using the update expression to which the extended back projection matrix is applied.

11. An image reconstruction method of reconstructing a tomographic image of an object using an iterative approximation method to apply matrices that are not transposed matrices of each other in forward projection processing and back projection processing, the method comprising:

a step of acquiring actual projection data of the object on the basis of scanning conditions; and a step of reconstructing the tomographic image by performing iterative approximation on the actual projection data using the scanning conditions and an update expression of the iterative approximation method including a relaxation coefficient that determines convergence of computation, wherein the relaxation coefficient is analytically calculated on the basis of the scanning conditions, and wherein, in the iterative approximation method, back projection processing using a view-direction weight is performed, and the computation unit reconstructs the tomographic image by calculating the view-direction weight to apply a weight of 0 excluding a predetermined number of views on both sides of a view of an X-ray tube position closest to an observed pixel in a body axis direction, calculating a back projection matrix applied as the back projection processing using the view-direction weight, and performing iterative approximation on the actual projection data using the update expression to which the back projection matrix is applied.

12. An image reconstruction method of reconstructing a tomographic image of an object using an iterative approximation method to apply matrices that are not transposed matrices of each other in forward projection processing and back projection processing, the method comprising:

a step of acquiring actual projection data of the object on the basis of scanning conditions; and a step of reconstructing the tomographic image by performing iterative approximation on the actual projection data using the scanning conditions and an update expression of the iterative approximation method including a relaxation coefficient that determines convergence of computation, wherein the relaxation coefficient is analytically calculated on the basis of the scanning conditions, wherein, in the iterative approximation method, the back projection processing is performed using extended projection data obtained by extending the actual projection data in a channel direction and/or a row direction and a view-direction weight, and reconstruction of the tomographic image is performed by calculating a transformation matrix from the actual projection data to the extended projection data on the basis of the scanning conditions, calculating the view-direction weight to apply a weight of 0 excluding a predetermined number of views on both sides of a view of an X-ray tube position closest to an observed pixel in a body axis direction, calculating an extended back projection matrix, which is applied as back projection processing in which the actual projection data and the extended projection data are combined, using the transformation matrix and the view-direction weight, and performing iterative approximation on the actual projection data and the extended projection data using the update expression to which the extended back projection matrix is applied.

* * * * *